United States Patent [19]

Robins

[11] Patent Number: 4,680,285
[45] Date of Patent: Jul. 14, 1987

[54] TREATMENT OF MALIGNANT TUMORS WITH 2-(β-D-RIBOFURANOSYLTHIAZOLE-4-CARBOXAMIDE RELATED COMPOUNDS

[75] Inventor: Roland K. Robins, Provo, Utah

[73] Assignee: Viratek, Inc., Costa Mesa, Calif.

[21] Appl. No.: 706,084

[22] Filed: Feb. 27, 1985

Related U.S. Application Data

[63] Continuation of Ser. No. 631,931, Jul. 18, 1984, abandoned, which is a continuation of Ser. No. 324,455, Nov. 24, 1981, abandoned, which is a continuation-in-part of Ser. No. 216,197, Dec. 15, 1980, abandoned.

[51] Int. Cl.$^4$ .................... A61K 31/70; C07H 5/00
[52] U.S. Cl. ........................... 514/23; 536/53; 536/55; 536/18.7
[58] Field of Search .............. 536/53, 55, 28, 29, 536/23; 514/23

[56] References Cited

U.S. PATENT DOCUMENTS 4,309,419  1/1982  Wolberg et al. ................ 536/24

OTHER PUBLICATIONS

Fuertes et al., Journal of Organic Chemistry, 1976, vol. 41, No. 29, pp. 4074–4077.
Srivastava et al., Journal of Medicinal Chemistry, 1977, vol. 20, No. 2, pp. 256–262.
Johnson, et al., Cancer Treatment Reviews (1975) 2, 1–31.

Primary Examiner—Johnnie R. Brown
Assistant Examiner—Elli Peselev
Attorney, Agent, or Firm—Herb Boswell

[57] ABSTRACT

The compound 2-β-D-ribofuranosylthiazole-4-carboxamide is used to treat malignant tumors in warm blooded animals. Esters of this compound such as 2-(2,3,5-tri-O-acetyl-β-D-ribofuranosyl)thiazole-4-carboxamide and 2-(5-O-phosphoryl-β-D-ribofuranosyl)thiazole-4-carboxamide are also useful for treating tumors in warm blooded animals.

16 Claims, No Drawings

TREATMENT OF MALIGNANT TUMORS WITH 2-(β-D-RIBOFURANOSYLTHIAZOLE-4-CARBOXAMIDE RELATED COMPOUNDS

CROSS REFERENCE TO RELATED APPLICATIONS

This application is a continuation of Ser. No. 06/631,931, filed July 18, 1984, now abandoned, which is a continuation of Ser. No. 06/324,455, filed Nov. 24, 1981, now abandoned, which is a continuation in part of my copending application Ser. No. 216,197 filed Dec. 15, 1980 now abandoned and entitled Treatment of Malignant Tumors with 2-β-D-Ribofuranosylthiazole-4-Carboxamide and Related Compounds, the entire disclosure of which is herein incorporated by reference.

BACKGROUND OF THE INVENTION

This invention is directed to a treatment of malignant tumors in vivo using the compound 2-β-D-ribofuranosylthiazole-4-carboxamide and related derivatives such as its esters.

Control of malignant tumors in man and animals still remains as an unrealized goal. Within the last several decades, understanding of malignancy has made significant progress; however, conquering of the malignant disease state has not been realized.

Conventional therapy of both humans and other valuable animal species inflicted with malignant tumors presently includes surgical excising of the tumor, local radiation therapy of the afflicted animal, and chemotheraphy by administration of a chemotheraputic agent to the animal. The death of a significant number of patients inflicted with malignant tumors is attributable not to the primary tumor but instead to metastasis of the primary tumor to secondary sites in the host. If a primary tumor is detected early, it normally can be eliminated by surgery, radiation or chemotheraphy or combinations of these. The metastatic colonies of these primary tumors, however, are exceedingly harder to detect and eliminate and the unsuccessful management of them remains a serious medical problem.

Tumors are normally classified either as benign or malignant. The malignant tumor is characterized from the benign by its ability to invade both surrounding tissue and to colonize distant sites via metastisis. Certain organs are more prone to metastasis than others. Included in this group would be the lung, the brain, the liver, the ovaries and the adrenal glands. It has further been suggested that both surgery and radiation of a primary tumor in certain instances actually promotes metastasis.

In view of the inability of current cancer therapy to successfully control the malignant tumor and its metastisis, it is evident that there exists a need for additional chemotheraputic agents.

In a paper entitled Synthesis and Antiviral Activity of Certain Thiazole C-Nucleosides, *J. Med. Chem.* 1977, Volume 20, No. 2, 256, I and my co-workers disclosed the synthesis of and certain preliminary in vitro antiviral activity of the compounds 2-β-D-ribofuranosylthiazole-4-carboxamide and 2-(2,3,5-tri-O-acetyl-β-D-ribofuranosyl)thiazole-4-carboxamide in an in vitro test system utilizing three viruses, type 1 herpes simplex virus, type 3 parainfluenza virus and type 3 rhinovirus. The in vitro activity of the compound 2-β-D-ribofuranosylthiazole-4-carboxamide against these three viruses was only moderate. With the compound 2-(2,3,5-tri-O-acetyl-β-D-ribofuranosyl)thiazole-4-carboxamide, only moderate activity was seen with type 1 herpes simplex virus whereas with the type 3 parainfluenza and the type 13 rhinoviruses activity was negative. While certain marginal in vitro antiviral activity noted in the preceding was seen, quite to the contrary, in vivo antiviral testing for both 2-β-D-ribofuranosylthiazole-4-carboxamide and 2-(2,3,5-tri-O-acetyl-β-D-ribofuranosyl)thiazole-4-carboxamide, as judged by the number of test animal deaths, was negative. In the in vivo tests, the number of deaths for the test animals for both 2-β-D-ribofuranosylthiazole-4-carboxamide and 2-(2,3,5-tri-O-acetyl-β-D-ribofuranosyl)thiazole-4-carboxamide was equal to or exceeded the number of deaths of the placebo control animals indicating that both of the compounds 2-β-D-ribofuranosylthiazole-4-carboxamide and 2-(2,3,5-tri-O-acetyl-β-D-ribofuranosyl)thiazole-4-carboxamide demonstrated no useful in vivo antiviral activity.

With regard to the above noted in vitro antiviral testing of both 2-β-D-ribofuranosylthiazole-4-carboxamide and 2-(2,3,5-tri-O-acetyl-β-D-ribofuranosyl)thiazole-4-carboxamide, these compounds were tested against viruses for which the known antiviral compound RIBAVIRIN ® is known to have positive antiviral acivity. In view of the preliminary marginal in vitro activity of 2-β-D-ribofuranosylthiazole-4-carboxamide against these test viruses, it was expected that the spectrum of activity of 2-β-D-ribofuranosylthiazole-4-carboxamide would be similar to the spectrum of activity of the compound RIBAVIRIN ®. RIBAVIRIN ® is known to be an active in vitro antiviral agent and in vivo antiviral and is further known to exhibit no significant antitumor activity. Additionally, certain derivatives of RIBAVIRIN ® such as its 5' monophosphate are also known to be inactive as antitumor compounds. It was reasonable to expect, in comparing the preliminary in vitro antiviral activity of 2-D-ribofuranosylthiazole-4-carboxamide with that of RIBAVIRIN ®, that 2-β-D-ribofuranosylthiazole-4-carboxamide would exhibit positive in vivo antiviral activity and negative antitumor activity similar to RIBAVIRIN ®. Totally contrary to this, the compound 2-β-D-ribofuranosylthiazole-4-carboxamide possessed no useful in vivo antiviral activity and, quite unexpectedly, has demonstrated positive antitumor activity.

I have found that the compound 2-β-D-ribofuranosylthiazole-4-carboxamide and its esters, including 2-(2,3,5-tri-O-acetyl-β-D-ribofuranosyl)-thiazole-4-carboxamide and 2-(5-O-phosphoryl-β-D-ribofuranosyl)thiazole-4-carboxamide exhibit antitumor activites of such significance as to be useful as antitumor agents in vivo.

BRIEF SUMMARY OF THE INVENTION

The compounds 2-β-D-ribofuranosylthiazole-4-carboxamide has been shown to exhibit significant antitumor activity in vivo. The present invention relates to the use of this compound and certain related derivatives in treating malignant tumors in warm blooded animals. According to this invention, the antitumor properties of 2-β-D-ribofuranosylthiazole-4-carboxamide and its related esters are utilized by administering to a warm blooded animal an effective amount of a pharmaceutical composition containing as the active compound at least about 0.1 percent by weight, based on the total weight of the composition, a compound of the structure:

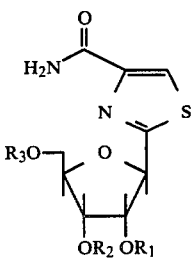

wherein $R_1$ and $R_2$ are H or $C_1$–$C_{18}$ acyl and $R_3$ is H, $C_1$–$C_{18}$ acyl or

and physiologically acceptable salts thereof. In a more preferred group of compounds $R_1$ and $R_2$ are H or $C_1$–$C_8$ acyl and $R_3$ is H, $C_1$–$C_8$ acyl or

and physiologically acceptable salts thereof.

Specifically noted for $R_1$, $R_2$ and $R_3$ as preferred acyl groups are acetyl, propionyl, butyryl, isobutyryl and benzoyl. Specifically noted as acceptable salts are the alkali metals and ammonium or substituted ammonium salts such as sodium, potassium and ammonium salts.

Preferrably, when $R_1$ and $R_2$ are H, $R_3$ is OH, $C_1$–$C_8$ acyl or

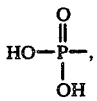

and when $R_1$ and $R_2$ is $C_1$–$C_8$ acyl, $R_3$ is $C_1$–$C_8$ acyl.

For use in the pharmaceutical composition of the invention, a pharmaceutical carrier would be utilized such that, preferredly, the pharmaceutical carrier would be chosen to allow administration of a suitable concentration of the active compounds of the invention as solutions or suspensions by injection into an afflicted warm blooded animal. Depending on the host harboring the malignant tumor, the type of tumor, and the tumor site, administration by injection would be intraveneously, intramuscularly, intracerebrally, subcutaneously, or intraperitoneally.

Alternately, the composition of the invention might suitably be formulated in appropriate pharmaceutical carriers allowing for administration by other routes such as oral administration, ophthalmic administration, topical administration or administration by suppository.

DETAILED DESCRIPTION

The parent compound of the invention, compound 2-β-D-ribofuranosylthiazole-4-carboxamide, is preferredly prepared as described in Example 1. An alternate synthesis of this compound appears in *J. Org. Chem.*, Vol. 41, No. 26, 1976, 4074, herein incorporated by reference.

Certain esters of 2-β-D-ribofuranosylthiazole-4-carboxamide, compound 1, such as 2-(2,3,5-tri-O-acetyl-β-D-ribofuranosyl)thiazole-4-carboxamide, compound 2, or 2-(5-O-phosphoryl-β-D-ribofuranosyl)thiazole-4-carboxamide, compound 3, are prepared as described in Examples 2 and 3 respectively. Additionally, other esters, such as the monoester 2-(5-O-acetyl-β-D-ribofuranosyl)thiazole-4-carboxamide, compound 4, would be prepared as in the synthesis described in example 4. For other preferred carboxylic esters of the invention substitution of acetic anhydride with a suitable anhydride such as propionic anhydride, butyric anhydride or benzoic anhydride is made. Alternately, the appropriate acid chloride could be substituted for the acid anhydride.

The esters of compound 1 could assist in delivery of the compound in an afflicted host. Such esters of the compound could be formed by reacting one or more of the hydroxyl groups of the sugar moiety of compound 1 with suitable reversible blocking groups which could be cleaved in vivo from the parent compound 1 by certain in situ chemical or enzymatic reactions.

For reaction with the hydroxyl groups, esters such as, but not necessarily limited to, acyl and phosphoryl esters would be considered. The acyl groups can be selected from a group consisting of straight chain, branch chain, substituted, unsaturated, saturated or aromatic acids such as, but not necessarily limited to, acetic, trifluoroacetic, propionic, n-butyric, isobutyric, valeric, caproic, pelargonic, enanthic, capyrlic, lactic, acrylic, propargylic, palmitic, benzoic, phthalic, salicylic, cinnamic and naphthoic acids. If a phosphoryl group is chosen, the phosphoryl ester could be as a free acid or as a salt form. Acceptable salts of the phosphate moiety of the phosphoryl ester can be selected from, but not necessarily limited to, the group consisting of alkali and alkaline earths, e.g., sodium, potassium, calcium, magnesium, lithium, ammonium and substituted ammonium, trialkylammonium, dialkylammonium, alkylammonium, e.g., triethylammonium, trimethylammonium, diethylammonium, octylammonium, cetyltrimethylammonium and cetylpyridium.

As preferred forms of the esters of the invention, compounds 2, 3 and 4 are mentioned. In addition to these, other tri-O-acyl esters such as the 2', 3', 5'-tri-O-benzoyl are mentioned. Additionally, other mono-esters such as the 5'-O-benzoyl is mentioned. Generally, for carboxylic esters the preferred esters would include $C_1$–$C_{18}$ acyls. A more preferred group includes $C_1$–$C_8$ acyls. Preferredly, when phosphoryl esters were utilized, the phosphate groups would be formed as a salt preferredly as a sodium salt or other alkali metal salt or ammonium.

Ester forms of compound 1, as is shown in the examples herein, are useful in delivering the compound to the affected site in an affected host. As is shown in the examples, the tri-acetyl ester, compound 2, is indicated as being an effective antitumor agent when injected intraperitoneally into an affected host. The described triacetyl compound and any other acyl ester of compound 1 would be expected to be hydrolized to compound 1 in certain biological fluids such as the acid environment of the stomach or an environment which includes an appropriate enzyme capable of in vivo enzymatic cleavage of the ester to compound 1. While I do not wish to be bound by theory, if the phosphoryl ester of compound 1, such as the 5' phosphate, were used, other enzymes present in vivo might also be expected to appropriately enzymatically cleave the phosphate to yield an in situ delivery of compound 1. Compound 3, the phosphoryl ester of compound 1, as is shown in the examples, is indicated as being an effective antitumor agent when injected in an effected host. At this time it is not known whether its activity is expressed as the 5' phosphate or whether it is enzymatically cleaved to compound 1. Further, it is possible that compound 1 might be promoted in situ by other enzymatic reactions to compound 3. In any event, both compound 1 and compound 3 are indicated as being effective in vivo antitumor agents as is indicated by the examples.

In performing the invention, compound 1, or a selected ester form thereof, is appropriately mixed with a suitable pharmaceutical carrier which may be as simple as sterilized water or could be a complex carrier having appropriate agents to suitably mimic certain biological environments, i.e., pH and salt adjusted solution suitable for intraveneous, intramuscular or other injections.

In selecting a suitable pharmaceutical carrier, consideration of the type of tumor, the site of the tumor and the health and age of the host would be given. Additionally, if an ester form of compound 1 is used, consideration of the chemical reactivity of the ester would also be given. Thus, carboxylic acyl ester would preferredly be suspended or solubilized in an appropriate non-acidic medium. A phosphoryl ester might be appropriately used in the presence of a suitable buffer or as a salt as discussed above.

Preferredly, compound 1 or any of the other compounds of the invention, would be mixed with an appropriate pharmaceutical carrier such that compound 1 or a derivative thereof would be suitably soluble in the carrier. Alternately, however, suspensions, emulsions and other formulations of the compounds of the invention could be used where indicated. The pharmaceutical carrier, in addition to having a solubilizing or suspending agent therein, might also include suitable dilutants, buffers, surface active agents and other similar agents as are typically used in pharmaceutical carriers. The total composition of the pharmaceutical carrier would, however, be chosen to be compatible with the site of delivery, the concentration of the active ingredient and other parameters as are standard in pharmaceutical industry.

Compound 1, or the other compounds of the invention, would be suitably admixed with the pharmaceutical carrier such that it would be present in a concentration of at least 0.1 percent by weight of the total composition. Preferredly, it would be present in the pharmaceutical carrier at a concentration of about 10% to about 90% by weight of the total composition.

Effective amounts of compound 1, or the other compounds of the invention, typically would range from about 2.5 milligrams per kilogram (mg/Kg) of the total body weight of the treated warm blooded animal to about 200 mg/Kg per day. Preferredly, the range would be from 12.5 mg/Kg to about 100 mg/Kg. An even more preferred range would be from about 15 mg/Kg to about 50 mg/Kg. As with other factors noted above, the amount of compound utilized in treating an afflicted animal would take into account parameters such as the type of tumor, the tumor site, the form of administering the compound and the physical size and condition of the host. In any event, the actual amount should be sufficient to provide a chemotherapeutically effective amount of the agent to the host in a convenient volume, which will be readily within the ability of those skilled in the art to determine given the disclosure herein.

In at least one study, compound 1 of the invention has been injected at dosages up to 2000 mg/Kg into tumor bearing animals and no deaths of the animals were attributed to the toxicity of compound 1 on the toxicity day of the test. In a host which has been diagnosed as being terminally ill with a malignant tumor excessive amounts beyond any toxicity range might be indicated if there is any probability of cure of the terminally ill host as is commonly practiced in current cancer chemotherapy.

As in the examples used for illustrative purposes below, wherein a tumor bearing host was treated once daily with the indicated test compound. Depending upon the clinical situation, the daily dose of compound 1 or any of the other compounds of the invention, might be similarly given; however, the daily does could also be broken up into sub-unit does which, in their totality, equal the daily dose. Thus, for example, at a 50 mg/Kg dose level the patient might be appropriately treated four times a day with doses of 12.5 mg/Kg.

A composition used for inhibiting malignant tumors in warm blooded animals might be suitably prepared by adding compound 1 or any of the other compounds of the invention, to a pharmacologically compatible solvent followed by sterilization and packaging in appropriate sealable vials at a known concentration. Appropriate doses of the compound are then withdrawn from the vial and administered by injection to the host.

EXAMPLE 1

2-$\beta$-D-Ribofuranosylthiazole-4-Carboxamide, COMPOUND 1

Ethyl 2-(2,3,5-tri-o-benzoyl-$\beta$-D-ribofuranosyl)-thiazole-4-carboxamide was utilized as prepared in Srivastova et. al, J. Med. Chem, 1977, Volume 20, No. 2, 256, herein incorporated by reference. A concentrated solution of ethyl 2-(2,3,5-tri-O-benzyl-$\beta$-D-ribofuranosyl)thiazole-4-carboxamide (5.0 g, 8.31 mmol) in methanol (15 ml) was stirred with methanolic ammonia (saturated at 0° C., 100 ml) in a pressure bottle at room temperature for 2 days. The solvent was evaporated and the residue was chromatographed through a column (2.5×35 cm) of silica gel (100 g) packed in ethyl acetate. Elution of the column with a solvent system (ethyl acetate-1-propanolwater, 4:1:2; v/v; top layer) removed the fast-moving methyl benzoate and benzamide. The slower moving, major, UV and sugar-positive fractions were collected and the solvent was evaporated in vacuo. The residue (syrup), thus obtained, was readily crystallized from ethanol-ethyl acetate to provide 1.6 g (74%) of pure product, compound 1: mp 144°–145° C.; $[\alpha]^{25}p$-14.3° (c 1, DMF); UV $\lambda_{max}^{pH1}$ 237 nm (8640); UV $\lambda_{max}^{pH11}$ 238 nm (8100); $^1$HNMR(Me$_2$SO-d$_6$) $\delta$ 7.5–7.8 [S(br), 2, CONH$_2$]$^1$HNMR (Me$_2$SO-d$_6$-D$_2$O) $\delta$ 4.99 (d, 1, J=5 Hz, H$_1'$), 8.25 (s, 1, H$_5$). Anal. (C$_9$H$_{12}$N$_2$O$_5$S) C, H, N, S.

EXAMPLE 2

2-(2,3,5-Tri-O-Acetyl-$\beta$-D-Ribofuranosyl)thiazole-4-Carboxamide, COMPOUND 2

Acetic anhydride (2.0 ml) was added to an ice-cold solution of compound 1 (1.04 g, 4 mmol) in anhydrous pyridine (16 ml) and the reaction solution was stirred at room temperature for 17 h. The solvent was evaporated in vacuo, the residue was dissolved in ethyl acetate, and the solution was washed with water and dried (MgSO$_4$). The ethyl acetate portion was evaporated in vacuo and the residue thus obtained was crystalized from water to provide 1.4 g (90%) of compound 2 as white needles; mp 103° C.; $^1$H NMR (CDCl$_3$) 2.1 (3 s, 9, tri-O-acetyl), 6.2 and 7.15 [pair of s(br), 2, CONH$_2$], 8.2 (s, 1, H$_5$). Anal. (C$_{15}$H$_{18}$N$_2$O$_8$S) C, H, N, S.

EXAMPLE 3

2-(5-O-Phosphoryl-$\beta$-D-Ribofuranosyl)thiazole-4 Carboxamide (2-$\beta$-D-Ribofuranosylthiazole-4-Carboxamide 5'-Phosphate), COMPOUND 3

Water (151 mg, 8.4 mmol) was added carefully to a solution (maintained at 0° C. with stirring) of freshly distilled phosphoryl chloride (2.0 g, 13.2 mmol), pyridine (1.21 g, 14.4 mmol) and acetonitrile (2.3 g, 56.7 mmol). 2-$\beta$-D-Ribofuranosylthiazole-4-carboxamide, compound 1, (dried over P$_2$O$_5$ and powdered, 800 mg, 3.0 mmol) was added to the solution and the reaction mixture was stirred continuously for 4 hrs at 0° C. The reaction mixture was poured into ice water (ca. 50 ml) and the pH was adjusted to 2.0 with 2N sodium hydroxide. The solution was applied to a column of activated charcoal (20 g), and the column was washed thoroughly with water until the eluate was salt-free. The column was eluted with a solution ethanol-water-concentrated ammonium hydroxide (10:10:1) and the fractions (25 ml each) were collected. The fractions containing pure (tlc, silica gel, acetonitrile-0.1N ammonium chloride (7:3)) nucleotide, compound 3, were collected and evaporated to dryness under vacuum. The anhydrous residue was dissolved in water and passed through a column of dowex 50W-X8 (20–50 mesh, H+ form, 15 ml). The column was washed with water and the fraction containing the nucleotide was collected. The solution was concentrated to a small volume (5 ml) and passed through a column of Dowex 50W-X8 (20–50 mesh, Na+ form, 15 ml). The column was washed with water. The nucleotide containing fraction was lyophilized. The residue was triturated with ethanol, collected by filtration and dried (P$_2$O$_5$), to provide 560 mg (47%) of compound 3 as monosodium dihydrate in the crystalline form.

Anal. calcd. for C$_9$H$_{12}$N$_2$O$_8$PSNa.2H$_2$O: C, 27.13; H, 4.04; N, 7.04; P, 7.78; S, 8.05. Found: C, 27.42; H, 3.87; N, 7.07; P, 8.03; S, 8.41.

EXAMPLE 4

2-(5-O-Acetyl-$\beta$-D-Ribofuranosyl)thiazole-4-carboxamide COMPOUND 4

A solution of 2-(2,3-O-isopropylidene-$\beta$-D-ribofuranosyl)thiazole-4-carboxamide (1.5 g, 5 mmol) (prepared as per Fuertes, et al, J. Org. Chem., Volume 41, NO. 26, 1976, 4074) in anhydrous pyridine (20 ml) was chilled in an ice-water bath and acetic anhydride (2.5 ml) was slowly added with stirring. The reaction solution was allowed to warm to room temperature and stirring was continued for 15 h. The solvent was evaporated in vacuo and the residue was dissolved in ethyl acetate and washed with water. The ethyl acetate portion was evaporated in vacuo and the residue was dissolved in 80% acetic acid (25 ml). The solution was heated on a steam bath for 30 mins. and the solvent evaporated in vacuo. The residue was dissolved in ethyl acetate, washed once with water and dried over Mg SO$_4$. The ethyl acetate portion was evaporated and the crude product was passed through a column of silica gel (100 g, packed in chloroform) and eluted with 20% (V/V) ethyl acetate in chloroform. The nucleoside bearing fractions were pooled and evaporated to yield 1.05 g (70%) of compound 4. (C$_{11}$H$_{14}$N$_2$O$_6$S).

As illustrative examples of the use of compound 1 and other illustrative compounds of the invention, examples 5 through 12, below, are given. In these examples, the efficacy of the compounds is demonstrated using the standard tests against certain malignant tumors. The tests utilized in these illustrative examples were conducted by the Developmental Therapeutics Program, Division of Cancer Treatment, National Cancer Institute. The tests were supervised by this agency utilizing their standard protocols and procedures. All tests conformed to these protocols and all tests were evaluated under the criteria defined by these protocols. The following representative examples illustrate confirmed activity of the illustrative compounds of the invention against screening tumor systems of the National Cancer Institute.

For purposes of the following examples, the abbreviation IP stands for intraperitoneal and IV stands for intravenous. The mean and median survival times are calculated in instruction 14 (revised 6/78) of the Screening Data Summary, Developmental Therapeutics Program, Division of Cancer Treatment, National Cancer Institute. The contents of this Screening Data Summary including appropriate revisions are herein incorporated by reference.

In the illustrated examples below, the vehicle used as carrier for the drug was injected (minus any drug therein) into the control animals at the same level of use of the vehicle in the drug treated animals in order to eliminate any vehicle effect of the tests.

EXAMPLE 5

As an indicator of reproducible activity, compound 1 of the invention was screened against L-1210 lymphoid leukemia in vivo using CD$_2$F$_1$ male mice as the testing species. The parameter of efficacy chosen was based upon the median survival time of animals treated with the drug vs. appropriate control group animals. Both drug treated animals and control group animals were inoculated IP with 10$^5$ seed cells of L-1210 lymphoid leukemia in Ascitic fluid.

One day after tumor inoculation, the drug group of animals was placed on a regimen of treatment of compound 1 at the dose levels as noted below, table 1. The drug treated group of animals was inoculated once daily for five days at the doses noted by IP injection of the test compound appropriately diluted with water.

Day six was chosen as an indication of drug toxicity. In this example, all drug treated animals survived through day six. Death of drug treated animals after day six was, therefore, attributed to tumor deaths and not drug toxicity.

The median death day of the control group was day 8.5. As noted in table 1 below, the median death day of the drug treated group was longer at all levels of drug tested and was significantly longer at greater than 50 mg/Kg (amount of drug/weight of test animal). The results shown in table 1 below indicate that in this multiple dose assay, the drug showed positive activity. A percent of drug treated animals/control animals greater than 125% is taken as positive drug activity.

TABLE 1

| Drug Dose mg/Kg | Treated Group Survival Time | Control Group Survival Time | Percent Treated Animals/ Control Animals |
|---|---|---|---|
| 200 | 14.3 | 8.5 | 168% |
| 100 | 12.7 | | 149% |
| 50 | 11.0 | | 129% |
| 25 | 10.2 | | 120% |
| 12.5 | 9.5 | | 111% |

EXAMPLE 6

Compound 2, 2-(2,3,5-tri-O-acetyl-$\beta$-D-ribofuranosyl)thiazole-4-carboxamide was screened in a manner similar to that shown in Example 5, however, the tumor system used as the test tumor was P388 lymphocytic leukemia. $10^6$ seed cells were used to initiate the tumor in both the control group and the drug treated group of animals. The same strain of mice was used except female mice were substituted for males. Test results were based on mean survival time and are expressed as T/C percentages (treated animals/control animals) as per Example 5.

In the drug treated animals, treatment was initiated one day after tumor inoculation and the drug was given at the dose levels noted below in table 2. Drug treatment was for nine days and drug toxicity, as in Example 5, was measured on day six. At the 100 mg/Kg level, one animal did not survive the toxicity cut-off date.

Average day of death for the control group was 10.2 days whereas at the lowest level of drug treatment the treated animals survived for more than 15 days. As with Example 5, 125% increase in longevity of treated animals over control animals was taken as indicative of positive drug response.

TABLE 2

| Drug Dose mg/Kg | Treated Group Survival Time | Control Group Survival Time | Percent Treated Animals/ Control Animals |
|---|---|---|---|
| 200 | 18.3 | 10.2 | 179% |
| 100 | 18.0 | | 176% |
| 50 | 15.3 | | 150% |

Compound 1 is also indicated as being active against P388 lymphocytic leukemia as per Examples 6a, b, and c, and 2-(2,3,5-tri-O-acetyl-$\beta$-D-ribofuranosyl)thiazole-4-carboxamide, compound 2, is indicated also as being active against P388 lymphocytic leukemia as per Example 7. In both of these examples, the compound successfully passed the DN 2 (Decision Network) criteria of the National Cancer Institute Testing. For examples 7 and 8, CD$_2$F$_1$ female mice were used and challenged with P388 lymphocytic leukemia tumors. The median survival time of the drug treated animals was compared to appropriate control animals and based on this criteria both of the compounds tested were considered as active antitumor agents. The test period was for thirty days in both Examples 7 and 8.

For Examples 7 and 8, as well as Examples 9 and 10 below, any animal of the drug treated group which survived beyond the end of the testing period was then evaluated and placed in one of three groups. The first group was designated as cured, meaning the animal was successfully cured of the tumor. The second group designation was no-takes, meaning survival of the animal was considered to be due to failure of tumor implant. The remaining group was designated as tumor survivors meaning the animals lived beyond the test cut-off date but could not be classified as either cured or no-takes.

For both Examples 7 and 8, thirty animals were used as the control group and six animals each were used at each dose level indicated in tables 3 and 4 below in the drug treated groups. In both Examples 7 and 8, for both the control group and the drug treated groups, tumors were induced by IP inoculation of tumor seed cells on day zero followed by initiation of drug treatment on day one. For both Examples 7a and 8, saline with tween/80 was used as the drug vehicle. For Examples 7b and 7c, water was used as the drug vehicle.

In both the control group and the drug treated group in Examples 7 and 8, the test animals were inoculated on day zero IP with $10^6$ seed cells of P388 lymphocytic leukemia. In both Examples 7 and 8, treatment of the drug group was started on day one and the drug was given IP once daily for nine days. Day six was utilized as the cut-off data for death attributable to toxicity of the drug. In only one instance, in Example 7b, was animal mortality attributed to drug toxicity. Efficacy of treatment was determined by comparing median survival time of the drug treated animals compared to median survival time of the control animals, and is expressed as percentage increase of treated animals/control animals (T/C) as per Example 5.

EXAMPLE 7a

In this example drug treated animals were injected IP with the dose level noted in Table 3 below. Six animals were treated at each dose level. No control animals survived beyond day 18 with a median death date of day 12.6. The median death day of the drug treated animals is as shown in Table 3a below. At the 50 mg/Kg level, one drug treated animal survived and was judged as a no-take.

EXAMPLE 7b

This examples was performed as per Example 7a at dose levels as noted in table 3b below. A survivor at both the 700 and 800 mg/Kg level was judged as cured. No controls survived beyond day 12 and the mean death day of the control group was day 11.

EXAMPLE 7c

This examples was run as per Example 7a above at dose levels noted in Table 3c below. All controls were dead by day 14 with a mean death day of day 11.9. At the 500 mg/Kg level, one animal was judged as a cure.

EXAMPLE 8

Compound 2, 2-(2,3,5-tri-O-acetyl-$\beta$-D-ribofuranosyl)thiazole-4-carboxamide was tested as per Example 7a above at dose levels noted in Table 4 below. No controls survived beyond day 18 with an average death date of day 12.6. At the 50 mg/Kg level, one surviving animal was judged as a no-take.

Both compounds 1 and 2 are indicated as being active antitumor agents in the multiple dose studies noted in Examples 7 and 8.

TABLE 3a

| Drug Dose mg/KG | Treated Group Survival Time | Control Group Survival Time | Percent Treated Animals/ Control Animals |
|---|---|---|---|
| 400 | 20.3 | 12.6 | 161% |
| 200 | 19.0 | | 150% |
| 100 | 18.3 | | 145% |

TABLE 3a-continued

| Drug Dose mg/KG | Treated Group Survival Time | Control Group Survival Time | Percent Treated Animals/ Control Animals |
|---|---|---|---|
| 50 | 15.3 | | 121% |
| 25 | 14.3 | | 113% |
| 12.5 | 13.9 | | 110% |

TABLE 3b

| Drug Dose mg/Kg | Treated Group Survival Time | Control Group Survival Time | Percent Treated Animals/ Control Animals |
|---|---|---|---|
| 800 | 27.0 | 11.0 | 245% |
| 700 | 27.0 | | 245% |
| 600 | 25.8 | | 234% |
| 500 | 21.8 | | 190% |
| 400 | 24.7 | | 224% |
| 300 | 21.8 | | 198% |

TABLE 3c

| Drug Dose mg/Kg | Treated Group Survival Time | Control Group Survival Time | Percent Treated Animals/ Control Animals |
|---|---|---|---|
| 800 | 11.8 | 11.9 | 99% |
| 700 | 10. | | 86% |
| 600 | 28.3 | | 237% |
| 500 | 25.0 | | 210% |
| 400 | 24.0 | | 201% |
| 300 | 23.0 | | 193% |

TABLE 4

| Drug Dose mg/Kg | Treated Group Survival Time | Control Group Survival Time | Percent Treated Animals/ Control Animals |
|---|---|---|---|
| 400 | 20.3 | 12.6 | 161% |
| 200 | 19.0 | | 150% |
| 100 | 18.3 | | 145% |
| 50 | 15.3 | | 121% |
| 25 | 14.3 | | 113% |
| 12.5 | 13.7 | | 110% |

Compound 1 is indicated as being active against L-1210 lymphoid leukemia as per Example 9, and successfully passed the DN 2 criteria of the National Cancer Institute testing. For Example 9a and 9b, $CD_2F_1$ male mice were used and challenged with L-1210 lymphoid leukemia. The mean survival time of the test animals was compared to appropriate control animals and based on this criteria, compound 1 was considered as an active antitumor agent. The test period was for thirty days. Test results are expressed as T/C as per Example 5.

In Example 9a, 24 control animals were used and six test animals at each drug dose level as is indicated below in table 9a. In Example 9b, forty control animals were used and ten test animals each at drug dose levels as shown in table 9b below. For both the control group and the drug test group, tumors were induced by IP inoculation of tumor seed cells on day zero followed by initiation of drug treatment on day one. For example 9a, water was used as the drug vehicle and for Examples 9b saline was used as the drug vehicle.

In both the control groups and the drug treated groups in Examples 9a and 9b, the test animals were inoculated on day zero IP with $10^6$ seed cells of L-1210 lymphoid leukemia. For Example 9a, drug treatment was started on day one and compound 1 given once daily for nine days. Day five was utilized as the cutoff date for death attributable to toxicity of the drug. In only one instance in Example 9b was mortality attributed to drug toxicity. Efficacy of treatment was determined by comparing mean survival time of drug treated animals with mean survival time of the control animals and is expressed as percentage increase of treated animals/control animals (T/C) as per Example 5.

EXAMPLE 9a

In this example, the drug treated animals were injected IP with dose levels noted in table 5a below. Six animals were treated at each dose level. No control animals survived beyond day ten with a mean death date of day 9.7. The mean death day of the drug treated animals is as shown in table 5a below.

EXAMPLE 9b

In this example, drug treated animals were injected IP with the dose level noted in table 5b below. Ten animals were treated at each dose level. No control animals survived beyond day ten with a mean death date of day 9.0. The mean death day of the treated animals is as shown in table 5b below.

TABLE 5a

| Drug Dose mg/Kg | Treated Group Survival Time | Control Group Survival Time | Percent Treated Animals/ Control Animals |
|---|---|---|---|
| 400 | 18.7 | 9.7 | 192% |
| 200 | 15.3 | | 157% |
| 100 | 14.0 | | 144% |
| 50 | 13.2 | | 136% |
| 25 | 12.8 | | 131% |

TABLE 5b

| Drug Dose mg/Kg | Treated Group Survival Time | Control Group Survival Time | Percent Treated Animals/ Control Animals |
|---|---|---|---|
| 800 | 15.4 | 9.0 | 171% |
| 600 | 20.7 | | 230% |
| 400 | 20.2 | | 224% |
| 200 | 16.4 | | 182% |
| 100 | 16.5 | | 183% |

Compound 1 is indicated as being active against Lewis lung carbinoma as per example 10 and successfully passed the DN 2 criteria of the National Cancer Institute Testing. For example 10, $B_6D_2F_1$ male mice were used and challenged with Lewis lung carcinoma. The median survival time of the test animals was compared to appropriate control animals and based on this criteria compound 1 was considered as an effective antitumor agent.

In Example 10, forty control animals were used and ten test animals each at dose levels indicated below in Table 6. For both the control group and the drug treated group, tumors were induced by IV injection on day zero followed by initiating of drug treatment on day one. For example 10 water was used as the drug vehicle.

In both the control group and the drug treated group in Example 10, the animals were inoculated on day zero with a homogenate of $10^6$ seed cells of Lewis lung carcinoma. For Example 10, drug treatment was started on day one and compound 1 given once daily for nine days. Day five was utilized as the cut-off date for details attributable to toxicity of the drug. There was no mortality attributable to drug toxicity in this example. Efficacy of treatment was determined by comparing median survival time of drug treated animals with median survival time of the control animals and is expressed as percentage increase of treated animals/control animals (T/C) as per Example 5.

The test period was for sixty days and at the end of the sixty day period all animals surviving in the test groups were evaluated as either cured, no-takes, or tumor survivors as per Example 5 above.

EXAMPLE 10

In this example, the drug treated animals were injected IP with the dose level noted in table 6 below. Ten animals were treated at each dose level. No control animals survived beyond day 23 with a median death data of day 18.4. At the test levels of 400, 200 and 25 mg/Kg all test animals survived the sixty day test period. Because of this fact, the T/C ratio noted in table 6 below is a constant figure based on assigning survival day rate of sixty to the treated animals and a median death date of 18.4 days to the control animals.

In Example 10 at both the 200 and 400 mg/Kg level, all ten surviving test animals were judged as cured. At the 100 mg/Kg level, there were eight cures and one tumor survivor with one death noted on day 46. At the 50 mg/Kg level, there were nine cures and one death on day 47.

Compound 1 is indicated as being an active antitumor agent in the multiple dose studies noted in Example 10.

TABLE 6

| Drug Dose mg/Kg | Treated Group Survival Time | Control Group Survival Time | Percent Treated Animals/ Control Animals |
|---|---|---|---|
| 400 | 60 | 18.4 | 326% |
| 200 | 60 |  | 326% |
| 100 | 60 |  | 326% |
| 50 | 60 |  | 326% |
| 25 | 60 |  | 326% |

As is shown in Example 10 above, compound 1 shows outstanding activity against Lewis lung carcinoma. Lewis lung carcinoma is an excellent examples of a metastatic tumor system. The tests and control animals of Example 10 were inoculated IV with a homogenate of the tumor. Dramatic expression of this tumor is then seen in the lungs. As was noted previously, the ability to metastasize is a property that uniquely characterizes a malignant tumor from a benign tumor. In Example 10, not only was the median survival time of drug treated animals dramatically extended but, at the cessation of the test period, except at one dose level, at least 80% cures were noted and at two of those levels 100% cures were present.

EXAMPLE 11

Compound 3, 2-(5-O-phosphoryl-$\beta$-D-ribofuranosyl)thiazole-4-carboxamide is indicated as being active against L-1210 lymphoid leukemia as per example 11a and 11b. These examples were performed essentially as per example 9 above except as noted. The compound test dosage levels are as noted in tables 7a and 7b below for Example 11a and 11b respectively. In these examples, thirty-six control animals were used and six test animals each at the drug dose levels as is shown in tables 7a and 7b. Saline was used as the drug vehicle. No drug toxicity was noted in the test animals for either examples 11a or 11b. No control animals survived beyond day 10 in example 11a with a mean death date of day 8.3 and beyond day eleven in example 11b with a mean death date of day 10.1.

For both the control groups and the drug test groups, tumors were induced by IP inoculation of tumor seed cells on day zero followed by initiation of drug treatment on day one wherein compound 3 was given once daily for 5 days. Test results are expressed as T/C as per example 5.

TABLE 7a

| Drug Dose mg/Kg | Treated Group Survival Time | Control Group Survival Time | Percent Treated Animals Control Animals |
|---|---|---|---|
| 800 | 16.3 | 8.3 | 196% |
| 400 | 15.2 |  | 183% |
| 200 | 21.5 |  | 259% |
| 100 | 15.5 |  | 186% |
| 50 | 11.3 |  | 136% |

TABLE 7b

| Drug Dose mg/Kg | Treated Group Survival Time | Control Group Survival Time | Percent Treated Animals Control Animals |
|---|---|---|---|
| 600 | 16.2 | 10.1 | 160% |
| 400 | 15.7 |  | 155% |
| 200 | 14.7 |  | 145% |
| 100 | 12.3 |  | 121% |
| 50 | 13.0 |  | 128% |

EXAMPLE 12

For Example 12, compound 1 was given IP to a group of AKD$_2$F$_1$ mice which were inflicted by intercranial inoculation with Lewis lung seed cells to establish brain tumors. The results in Table 8 below indicate that the IP inoculation of the afflicated animals with compound 1 resulted in reduction of the brain tumors indicating successful crossing of the blood brain barrier by compound 1 following the IP injection into the afflicated animals.

For this test, 32 control animals were used and no control animals survived beyond day eleven with a mean death data of day 9.6 for the controls. Eight test animals were used for each drug dose level with the exception of the 300 mg/Kg level as is shown in table 8 below. Water was used as the drug vehicle. For both the control group and the test group, tumors were induced on day zero with initiation of drug treatment on day one where compound 1 was given once daily for nine days. Test results are expressed as T/C as per example 5.

TABLE 8

| Drug Dose mg/Kg | Treated Group Survival Time | Control Group Survival Time | Percent Treated Animals/ Control Animals |
|---|---|---|---|
| 800 | 21.3 | 9.6 | 221% |
| 700 | 20.3 |  | 211% |
| 600 | 20.3 |  | 211% |
| 300 | 20.5 |  | 213% |
| 150 | 20.5 |  | 197% |
| 75 | 19.0 |  | 185% |
| 37.5 | 16.0 |  | 166% |
| 25.0 | 16.6 |  | 172% |

In a significant number of disease states of the brain of both pathogenic and host dysfunction origins, treatment is inhibited by the lack of drug transfer across the blood brain barrier. In certain instances wherein appropriate treatment of a disease state is known, complications can arise in treating these diseases when they are located intercranially because of the lack of transfer across the blood brain barrier of effective concentrations of appropriate chemotheraputic agents. The indication, as seen in table 8, that compound 1 successfully crosses the blood brain barrier is thus very promising for the treatment of brain tumors.

The following representative examples, 13 through 17, are given for the formulations of the active compound of the invention in illustrative pharmaceutical compositions utilizing illustrative carriers. In these examples, example 13 illustrates the use of the compounds of the invention in injectables suitable for intravenous or other types of injection into the host animal. Example 14 is directed to an oral syrup preparation, Examples 15 to an oral capsule preparation and Example 16 to oral tablets. Example 17 is directed to use of the compounds of the invention in suitable suppositories. For example 13 through 17 the ingredients are listed followed by the methods of preparing the composition.

EXAMPLE 13

| INJECTABLES Example 13a Compound 1 | |
|---|---|
| Compound 1 | 250 mg–1000 mg |
| Water for Injection USP q.s. | |

Compound 1 is dissolved in the water and passed through a 0.22µ filter. The filtered solution is added to ampoules or vials, sealed and sterilized.

| Example 3b Compound 3 | |
|---|---|
| Compound 3 as a Sodium Salt | 250 mg–1000 mg |
| Water for Injection USP q.s. | |

Prepared as per Example 3a, above.

EXAMPLE 14

| SYRUP Example 14a Compound 1 250 mg Active ingredient/5 ml syrup | |
|---|---|
| Compound 1 | 50 g |
| Purified Water USP | 200 ml |
| Cherry Syrup q.s. or | 1000 ml |

Compound 1 is dissolved in the water and to this solution the syrup is added with mild stirring.

| Example 14b Compound 3 250 mg Active Ingredient/5 mls syrup | |
|---|---|
| Compound 3 as a Sodium Salt | 50.0 g |
| Purified Water USP q.s. or | 200 ml |
| Cherry Syrup q.s. ad | 1000 ml |

Prepared as per Example 14a above.

EXAMPLE 15

| CAPSULES Example 15a Compound 1 100 mg, 250 mg or 500 mg | |
|---|---|
| Compound 1 | 500 g |
| Lactose USP, Anhydrous q.s. or | 200 g |

| -continued CAPSULES Example 15a Compound 1 100 mg, 250 mg or 500 mg | |
|---|---|
| Sterotex Powder HM | 5 g |

Combine compound 1 and the Lactose in a twin-shell blender equipped with an intensider bar. Tumble blend for two minutes, followed by blending for one minute with the intensifier bar and then tumble blend again for one minute. A portion of the blend is then mixed with the Sterotex Powder, passed through a #30 screen and added back to the remainder of the blend. The mixed ingredients are then blended for one minute, blended for the intensifier bar for thirty seconds and tumble blended for an additional minute. Appropriate sized capsules are filled with 141 mg, 352.5 mg or 705 mg of the blend, respectively, for the 100 mg, 250 mg and 500 mg containing capsules.

EXAMPLE 15b

| Example 15b Compound 2 100 mg, 250 mg or 500 mg | |
|---|---|
| Compound 2 | 500 g |
| Lactose USP, Anhydrous q.s. or | 200 g |
| Sterotex Powder HM | 5 g |

Mix and fill as per Example 15a.

| Example 15c Compound 4 100 mg, 250 mg or 500 mg | |
|---|---|
| Compound 4 | 500 g |
| Lactose USP, Anhydrous q.s. or | 200 g |
| Sterotex Powder HM | 5 g |

Mix and fill as per Example 15a.

EXAMPLE 16

| TABLETS Example 16a Compound 1 100 mg, 200 mg or 500 mg | |
|---|---|
| Compound 1 | 500 g |
| Corn Starch NF | 200.0 g |
| Cellulose Microcrystalline | 46.0 g |
| Sterotex Powder HM | 4.0 g |
| Purified Water q.s. or | 300.0 ml |

Combine the corn starch, the cellulose and Compound 1 together in a planetary mixer and mix for two minutes. Add the water to this combination and mix for one minute. The resulting mix is spread on trays and dried in a hot air oven at 50° C. until a moisture level of 1 to 2 percent is obtained. The dried mix is then milled with a Fitzmill through a #RH2B screen at medium speed. The Sterotex Powder is added to a portion of the mix and passed through a #30 screen, and added back to the milled mixture and the total blended for five minutes by drum rolling. Compressed tables of 150 mg, 375 mg and 750 mg respectively, of the total mix are formed with appropriate sized punches for the 100 mg, 250 mg or 500 mg containing tables.

EXAMPLE 17

| SUPPOSITORIES | | | |
|---|---|---|---|
| Example 17a Compound 1 | | | |
| 250 mg, 500 mg or 1000 mg per 3 g | | | |
| Compound 1 | 250 mg | 500 mg | 1000 mg |
| Polyethylene Glycol 1540 | 1925 mg | 1750 mg | 1400 mg |
| Polyethylene Glycol 8000 | 825 mg | 750 mg | 600 mg |

Melt the Polyethylene Glycol 1540 and the Polyethylene Glycol 8000 together at 60° C. and dissolve Compound 1 into the melt. Mold this total at 25° C. into appropriate suppositories.

| Example 17b Compound 2 | | | |
|---|---|---|---|
| 250, 500, 1000 mg per 3 g | | | |
| Compound 2 | 250 mg | 500 mg | 1000 mg |
| Polyethylene Glycol 1540 | 1925 mg | 1750 mg | 1400 mg |
| Polyethylene Glycol 8000 | 825 mg | 750 mg | 600 mg |

Prepare as per Example 17a Above.

I claim:

1. A method of treating tumors in warm blooded animals comprising:
administering to said warm blooded animals an effective amount of a pharmaceutical composition containing as the active component at least about 0.1 percent by weight, based on the total weight of the composition, a compound of the structure:

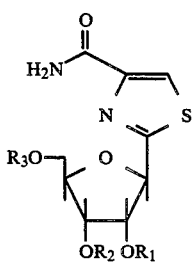

wherein $R_1$ and $R_2$ are H or $C_1$-$C_{18}$ acyl and $R_3$ is H, $C_1$-$C_{18}$ acyl or

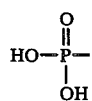

and physiologically acceptable salts thereof.

2. The method of claim 1 wherein:
$R_1$ and $R_2$ are H or $C_1$-$C_8$ acyl and $R_3$ is H, $C_1$-$C_8$ acyl or

and physiologically acceptable salts thereof.

3. A method of treating tumors in warm blooded animals comprising:
administering to said warm blooded animals an effective amount of a pharmaceutical composition containing as the active component at least 0.1 percent by weight, based on the total weight of the composition, a compound selected from the group consisting of 2-$\beta$-D-ribofuranosylthiazole-4-carboxamide, 2-(2,3,5-tri-O-acetyl-$\beta$-D-ribofuranosyl)thiazole-4-carboxamide and 2-(5-O-phosphoryl-$\beta$-D-ribofuranosyl)thiazole-4-carboxamide and physiologically acceptable salts thereof.

4. The method of claim 3 wherein said compound is 2-$\beta$-D-ribofuranosylthiazole-4-carboxamide.

5. The method of claim 3 wherein said compounds is 2-(2,3,5-tri-O-acetyl-$\beta$-D-ribofuranosyl)thiazole-4-carboxamide.

6. The method of claim 3 wherein said compound is 2-(5-O-phosphoryl-$\beta$-D-ribofuranosyl)thiazole-4-carboxamide and physiologically acceptable salts thereof.

7. The method of claim 3 wherein:
said active component is given to said warm blooded animals at a dosage of at least 2.5 milligrams of the active component per kilogram of the body weight of the warm blooded animals.

8. The method of claim 7 wherein:
said active component is administered to said warm blooded animals at a dosage of from about 12.5 to about 100 milligrams of the active component per kilogram of body weight of the warm blooded animals.

9. The method of claim 3 wherein:
said pharmaceutical composition is administered by injection.

10. The method of claim 3 wherein:
said active compound is present in said pharmaceutical composition at a concentration of about 10% to about 90% by weight of the total composition.

11. An antitumor composition for the treatment of tumors in vivo containing as its active ingredient an effective amount of a compound selected from the group consisting of acyl and phosphoryl ester derivatives of 2-beta-D-ribofuranosylthiazole-4-Carboxamide and physiologically acceptable salts thereof, provided that said compound is not the 2,3,5-tri-O-acetyl ester derivative.

12. The composition of claim 11 wherein:
said compound is an acyl ester derivative of 2-$\beta$-D-ribofuranosylthiazole-4-carboxamide.

13. The composition of claim 12 wherein said acyl ester is an acetate ester.

14. The composition of claim 12 wherein said acyl ester is a benzoate ester.

15. The composition of claim 11 wherein:
said compound is a phosphoryl ester of 2-$\beta$-D-ribofuranosylthiazole-4-carboxamide.

16. The compound 2-$\beta$-D-ribofuranosylthiazole-4-carboxamide 5'-phosphate.

* * * * *

UNITED STATES PATENT AND TRADEMARK OFFICE
CERTIFICATE OF CORRECTION

PATENT NO. : 4,680,285
DATED : JULY 14, 1987
INVENTOR(S) : ROLAND K. ROBINS

Page 1 of 2

It is certified that error appears in the above-identified patent and that said Letters Patent is hereby corrected as shown below:

In the title, "2-($\beta$-D-RIBOFURANOSYLTHIAZOLE-4-CARBOXAMIDE" should be --2-$\beta$-D-RIBOFURANOSYLTHIAZOLE-4-CARBOXAMIDE--, Column 2, line 39, "2-D-ribofuranosylthiazole-4-carboxamide" should be --2-$\beta$-D-ribofuranosylthiazole-4-carboxamide--, Column 2, line 57, "compounds" should be --compound--, Column 5, line 27, "Thus," should be --Thus a--, Column 6, lines 18 and 19, "does" should be --doses--, Column 6, line 48, "acetate-1-propanolwater" should be --acetate-1-propanol water--, Column 7, line 11, insert a --,-- after "Carboxamide", Column 7, line 13, delete the --,-- between "5'-Phosphate)" and "COMPOUND 3", Column 12, line 64, "details" should be --deaths--, Column 13, line 14, "data" should be --date--, Column 13, line 42, "examples" should be --example--,

UNITED STATES PATENT AND TRADEMARK OFFICE
CERTIFICATE OF CORRECTION

PATENT NO. : 4,680,285
DATED : JULY 14, 1987
INVENTOR(S) : ROLAND K. ROBINS

It is certified that error appears in the above-identified patent and that said Letters Patent is hereby corrected as shown below:

```
Column 15, line 31, "0.22ufilter" should be --0.22u filter--
Column 16, line 9, "intensider" should be --intensifier--,
Column 16, line 16, "blended for" should be --blended with--,
Column 16, lines 65 and 68, "tables" should be --tablets--,
Column 18, line 22, "Compounds" should be --Compound--, and
Column 18, line 43, "Compound" should be --component--.
```

Signed and Sealed this

Seventh Day of June, 1988

Attest:

DONALD J. QUIGG

Attesting Officer

Commissioner of Patents and Trademarks